(12) United States Patent
Moore

(10) Patent No.: US 7,935,097 B1
(45) Date of Patent: May 3, 2011

(54) COLOSTOMY BAG BELT

(76) Inventor: Marcella L. Moore, Florissant, MO (US)

( * ) Notice: Subject to any disclaimer, the term of this patent is extended or adjusted under 35 U.S.C. 154(b) by 640 days.

(21) Appl. No.: 11/968,355

(22) Filed: Jan. 2, 2008

(51) Int. Cl.
*A61F 5/44* (2006.01)
(52) U.S. Cl. ......... 604/345; 604/333; 604/343; 604/344
(58) Field of Classification Search .......... 604/332–345, 604/174, 178, 264, 96.01, 180, 93.01, 280, 604/282, 103.12, 164
See application file for complete search history.

(56) References Cited

U.S. PATENT DOCUMENTS

| | | | |
|---|---|---|---|
| 3,773,048 A | 11/1973 | Kirkliauskas | |
| 3,948,256 A | 4/1976 | Schneider | |
| 4,738,661 A | 4/1988 | Marut | |
| 5,653,701 A | 8/1997 | Millman | |
| 5,947,942 A | 9/1999 | Galjour | |
| D418,221 S | 12/1999 | Betts et al. | |

*Primary Examiner* — Jacqueline F. Stephens

(57) ABSTRACT

This patent discloses a colostomy bag belt to be worn by a person to help secure a colostomy bag to that person in an environment. The colostomy bag belt may include a liquid permeable layer fixed against a liquid impermeable layer to form a waste channel. An absorbent core may be located in the waste channel. The colostomy bag belt may include a colostomy bag hole and the absorbent core may be exposed to the environment through a belt top, belt bottom, and a perimeter of the colostomy bag hole. An adhesive layer may be located on the liquid permeable layer around the hole to adhere to the colostomy bag.

7 Claims, 5 Drawing Sheets

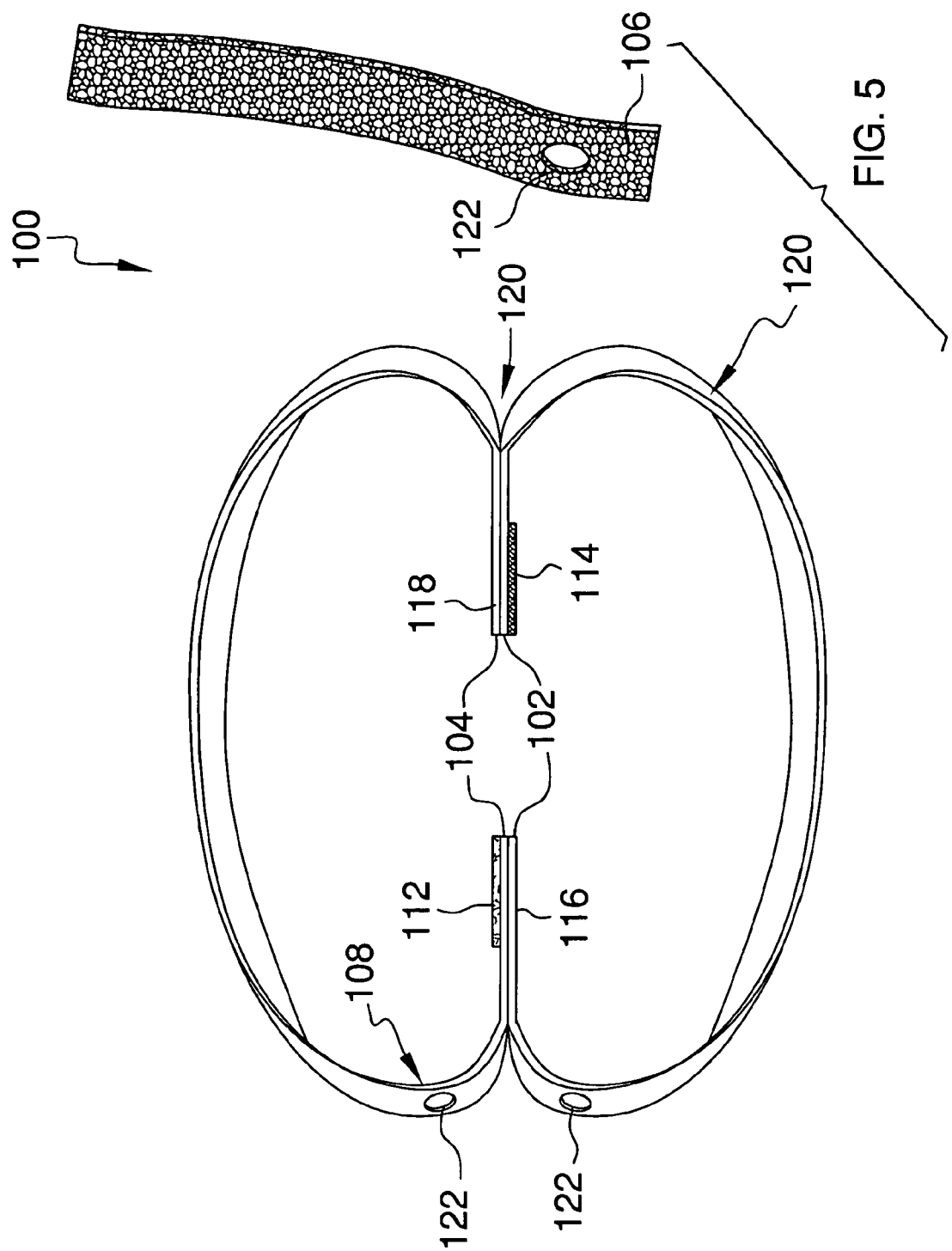

COLOSTOMY BAG BELT

BACKGROUND

1. Field

The information disclosed in this patent relates to a belt that may be worn by a person to help secure a colostomy bag to that person.

2. Background Information

A colostomy is a surgical procedure that involves connecting a part of the colon onto the anterior abdominal wall. There are many reasons for this procedure: a section of the colon has had to be removed, for example due to colon cancer, diverticulitis, injury, etc., so that it is no longer possible for feces to pass out via the anus; or a portion of the colon has been operated upon and needs to be rested until it is healed. In the latter case, the colostomy is often temporary and may be reversed later, leaving the patient with a small scar where the stoma was.

A colostomy leaves the patient with an opening on the abdomen called a stoma. This opening is formed from the end of the large intestine drawn out through the incision and sutured to the skin. After a colostomy, feces leave the patient's body through the stoma. People with colostomies use an external pouch (bag) to collect intestinal waste (feces) that comes from the stoma. It is difficult to secure the bag to the stoma and waste sometimes spills out of the stoma and bag. It is desirable to overcome these and other problems.

SUMMARY

This patent discloses a colostomy bag belt to be worn by a person to help secure a colostomy bag to that person in an environment. The colostomy bag belt may include a liquid permeable layer fixed against a liquid impermeable layer to form a waste channel. An absorbent core may be located in the waste channel. The colostomy bag belt may include a colostomy bag hole and the absorbent core may be exposed to the environment through a belt top, belt bottom, and a perimeter of the colostomy bag hole. An adhesive layer may be located on the liquid permeable layer around the hole to adhere to the colostomy bag.

BRIEF DESCRIPTION OF THE FIGURES

FIG. 5 is an isometric view of belt 100 everted and absorbent core 106 remote from belt 100.

DETAILED DESCRIPTION

Figure 1:
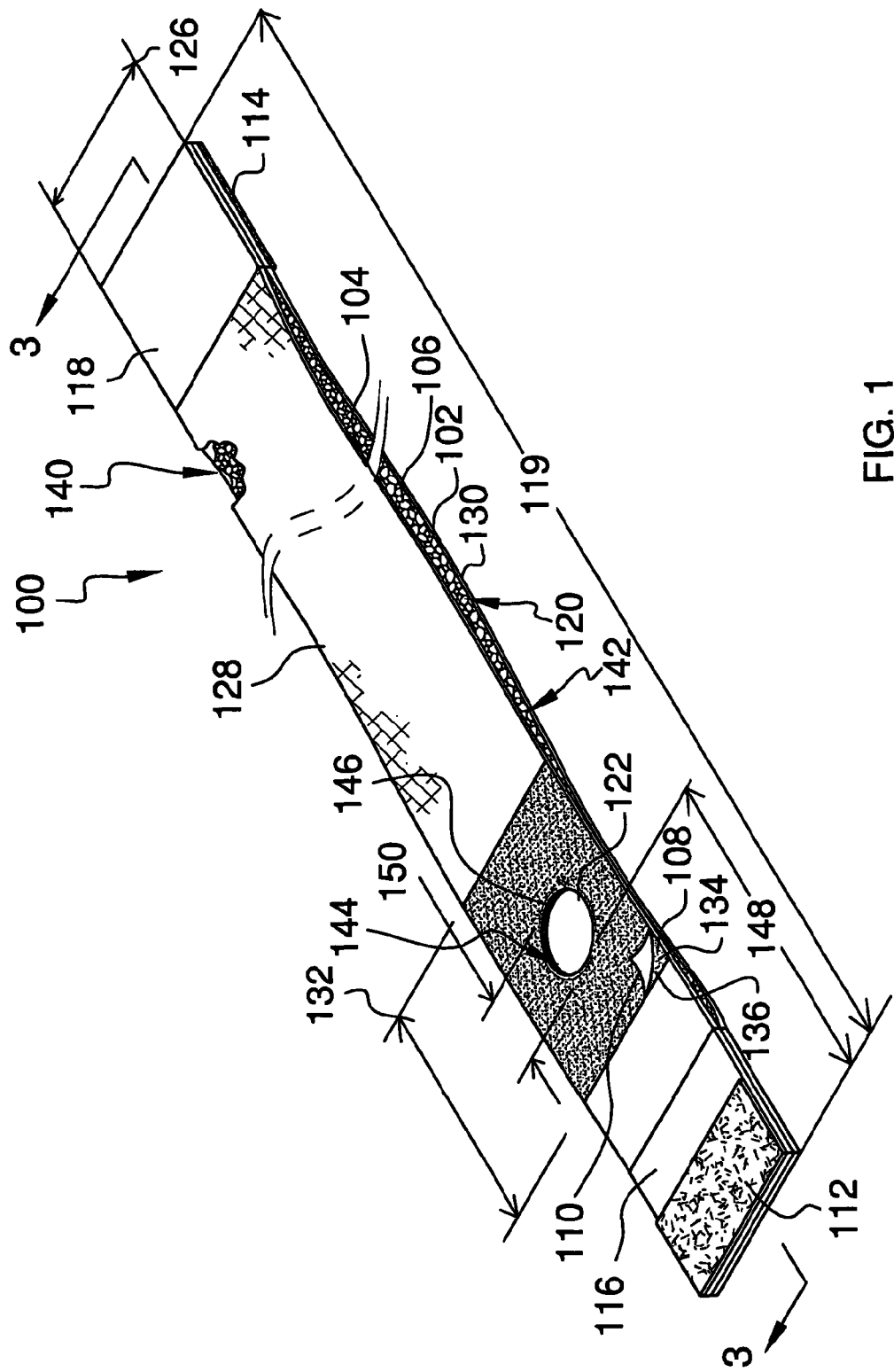
FIG. 1 is an isometric top view of a belt 100.
Figure 2:
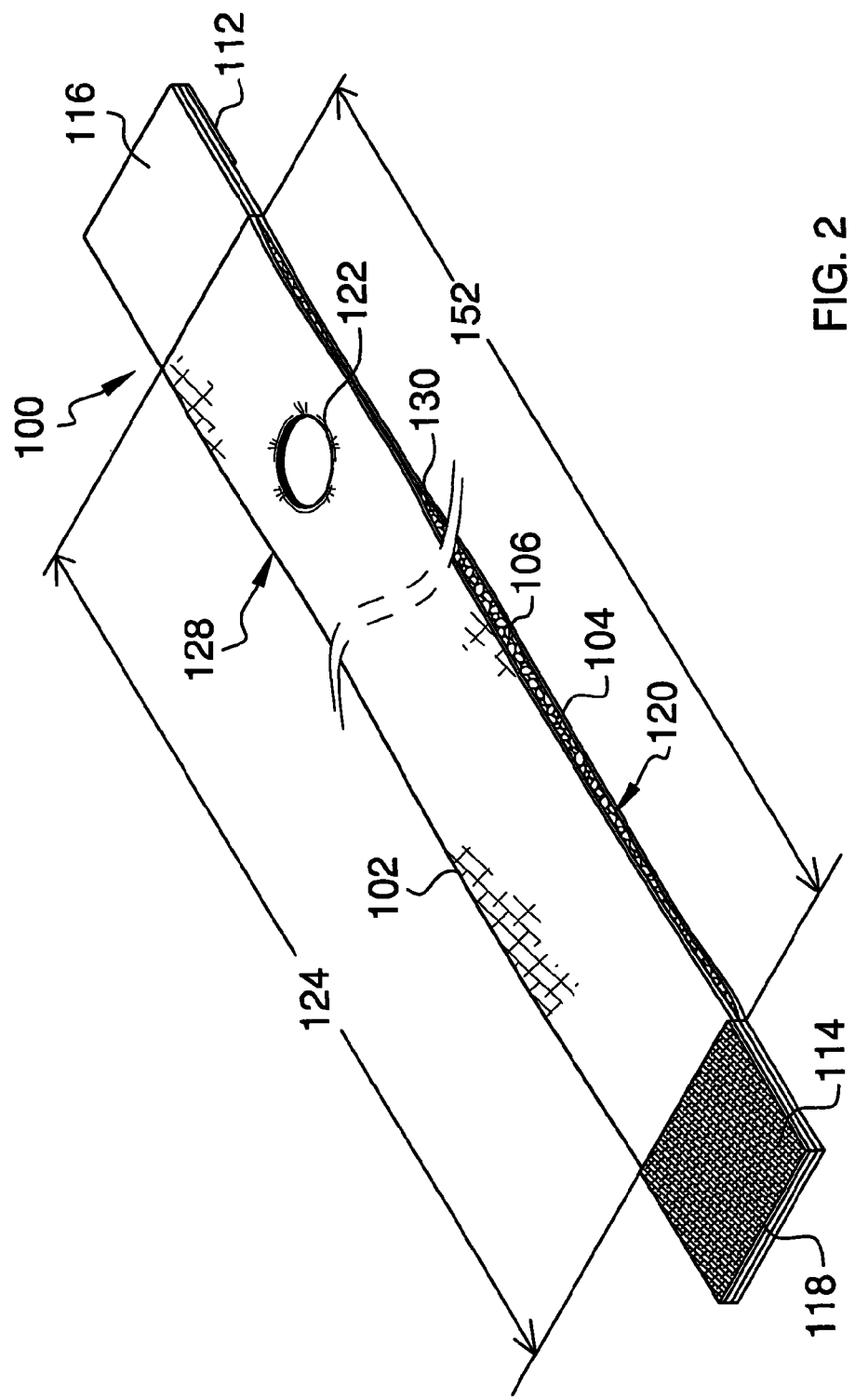
FIG. 2 is an isometric bottom view of a belt 100.

FIG. 1 is an isometric top view of a belt 100. FIG. 2 is an isometric bottom view of a belt 100. Belt 100 may be a loop of material that may be worn by a person 10 (FIG. 4) to help secure a colostomy bag 12 (FIG. 4) to person 10 in an environment 14. Colostomy bag 12 may be part of a pouching system that may aid in the collection of waste from a diverted biological system. Colostomy bag 12 may attach to the exterior opening of a colostomy (stoma) and to belt 100 to permit sanitary collection of bodily wastes and be removed from the stoma and belt 100 to permit sanitary disposal of bodily wastes. Belt 100 may work to secure colostomy bag 12 to person 10, absorb spillage from the stoma and colostomy bag 12, and hide waste odors.

Figure 3:
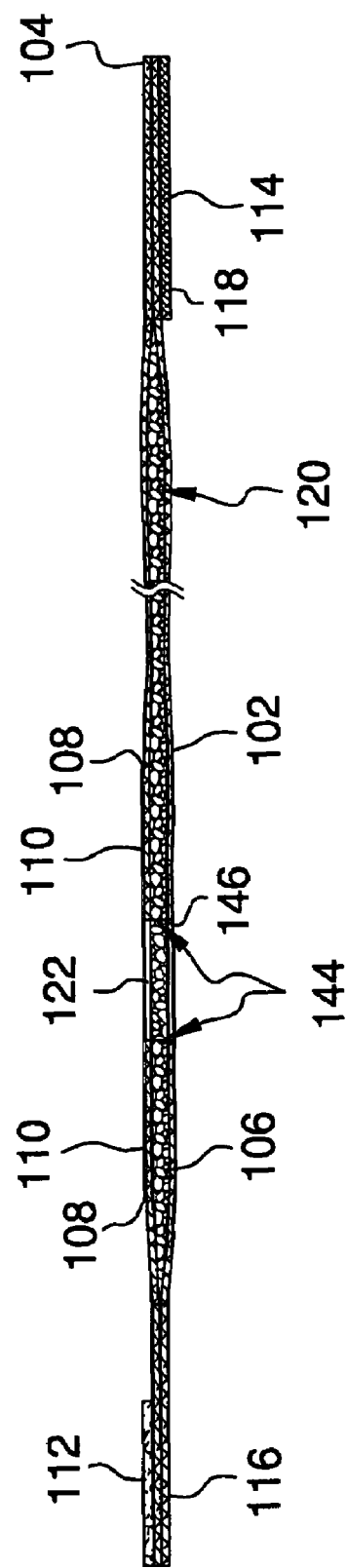
FIG. 3 is a section view of belt 100 generally taken off line 3-3 of FIG. 1.

FIG. 3 is a section view of belt 100 generally taken off line 3-3 of FIG. 1. Belt 100 may include a liquid impermeable layer 102, a liquid permeable layer 104, absorbent core 106, an adhesive layer 108, an adhesive backing 110, a first hook and loop fastener 112, and a second hook and loop fastener 114. Liquid permeable layer 104 may be fixed against liquid impermeable layer 102 at a belt first end 116 and at a belt second end 118 to form a waste channel 120 between belt first end 116, belt second end 118, liquid impermeable layer 102, and liquid permeable layer 104. Belt 100 may have a belt length 119 extending from a tip of belt first end 116 to a tip of belt second end 118. In one example, belt length 119 substantially may be 23 to 40 inches in length. Belt first end 116 and belt second end 118 each may have a length approximately of three inches.

First hook and loop fastener 112 may be attached to liquid permeable layer 104 at belt first end 116. Second hook and loop fastener 114 may be attached to liquid impermeable layer 102 at belt second end 118. Absorbent core 106 may be located in waste channel 120. Adhesive layer 108 and adhesive backing 110 may be stacked on liquid permeable layer 104. Belt 100 additionally may include a colostomy bag hole 122.

Liquid impermeable layer 102 may include a woven or non-woven, strong textile configured to provide the support for colostomy bag 12 hanging from colostomy bag hole 122. Liquid impermeable layer 102 may reside against a stomach 18 (FIG. 4) of person 10. It may be undesirable to have waste spillage touch stomach 18. Liquid impermeable layer 102 may be hydrophobic. In addition, liquid impermeable layer 102 may include a sealing material such as polyethylene to act as a barrier between stomach 18 of a wearer 10 of belt 100 and waste spillage absorbed into belt 100. Liquid impermeable layer 102 may have a liquid impermeable layer length 124 (FIG. 2) as measured between belt first end 116 and belt second 118 and a liquid impermeable layer width 126 (FIG. 1) extending between a belt top 128 and a belt bottom 130. In one example, liquid impermeable layer length 124 substantially may be 17 to 34 inches in length and liquid impermeable layer width 126 substantially may be 8-inches in width.

Liquid permeable layer 104 may include a non-woven textile that may allow waste spillage to pass through liquid permeable layer 104. In addition, liquid permeable layer 104 may be capable of returning to its original shape after being stretched so that it may expand to allow additional waste spillage to be absorbed by absorbent core 106. In one example, liquid permeable layer 104 may include an elastic net embedded in a liquid permeable, non-woven material.

As noted above, liquid permeable layer 104 may be fixed against liquid impermeable layer 102 at a belt first end 116 and a belt second end 118. Liquid permeable layer 104 and liquid impermeable layer 102 are not otherwise attached to one another. In one example, liquid permeable layer 104 may be sewn to liquid impermeable layer 102 in a rectangular pattern at belt first end 116 and at belt second end 118, where the two rectangular patterns may be remote from each other. In another example, liquid permeable layer 104 may be glued to liquid impermeable layer 102 at belt first end 116 and belt second end 118. In another example, a first and second cap may be compressed or shrunk fit around belt first end 116 and belt second end 118, respectively, to secure liquid permeable layer 104 to liquid impermeable layer 102 at belt first end 116 and belt second end 118.

Absorbent core 106 may be a layer of material configured to absorb waste spillage from a colostomy bag and a stoma. Absorbent core 106 may include cellulosic absorbent material, such as a plastic made from cellulose or a derivative of cellulose. Absorbent core 106 may include fluff pulp, wood pulps, defiberised wood pulp, and super absorbent fibers. Fluff pulp may include wood that has been ground to a pulp, where the fibers may be loose relative to each other. Absorbent core 106 may include an odor absorbing/masking agent.

Adhesive layer 108 may be a flat, rectangular shape layer extending from belt top 128 to belt bottom 130. Adhesive layer 108 may have an adhesive layer length 132. Adhesive layer 108 may include glue, paste, mastic, or other sticky substance to bond a colostomy bag to belt 100.

Adhesive layer 108 may be large enough to mate with various colostomy bags. However, different colostomy bag designs may utilize different areas of adhesive layer 108 because of the bags design. Thus, there may be areas of adhesive layer 108 not secured to a colostomy bag that may remain exposed. It may be desirable that these exposed adhesive layer 108 areas have liquid permeable properties to permit waste spillage to pass through adhesive layer 108.

Adhesive layer 108 may include a pattern of adhesive layer holes 134 to permit waste spillage to pass through adhesive layer 108 and into liquid permeable layer 104. Each adhesive layer hole 134 may have an adhesive layer hole diameter 136. In one example, there may be an average of sixteen adhesive layer holes 134 per square inch of adhesive layer 108, where each adhesive layer hole diameter 136 may measure approximately 0.1-inch diameter. In another example, adhesive layer 108 may include a liquid permeable adhesive material.

Adhesive backing 110 may be a pressure sensitive release paper or film attached to adhesive layer 108 to protect adhesive layer 108 prior to use. Adhesive backing 110 may be the same size and shape as adhesive layer 108. In operation, adhesive backing 108 may be pealed away from adhesive layer 108 to expose adhesive layer 108.

First hook and loop fastener 112 and second hook and loop fastener 114 may meet together to form an attachment 138 (FIG. 4) that may secure together belt first end 116 and belt second end 118. Attachment 138 may have a hook side that includes a piece of fabric covered with tiny plastic hooks, and a loop side that includes a piece of fabric covered with plastic loops. When first hook and loop fastener 112 and second hook and loop fastener 114 are pressed together, the hooks may catch in the loops and belt first end 116 and belt second end 118 together. Attachment 138 may be broken by pulling apart first hook and loop fastener 112 and second hook and loop fastener 114.

Waste channel 120 may be a space between liquid impermeable layer 102 and liquid permeable layer 104 to receive waste spillage from the stoma and colostomy bag 12. Waste channel 120 may extend between where liquid permeable layer 104 is fixed against liquid impermeable layer 102. Waste channel 120 may extend between belt first end 116 and belt second end 118. Absorbent core 106 may fill the space provided by waste channel 120 so that waste liquid entering waste channel 120 may be collected by absorbent core 106.

Any waste spillage that does not enter waste channel 120 ends up on person 10, on the clothes of person 10, and/or on the floor. In addition to causing an embarrassing mess, the uncollected waste spillage typically has a foul odor. It is desirable to promote waste spillage entering waste channel 120.

Waste channel 120 may have a first waste channel opening 140 at belt top 128 between belt first end 116 and belt second 118, a second waste channel opening 142 at belt bottom 130 between belt first end 116 and belt second 118, and a third a waste channel opening 144 (FIG. 3) around a colostomy bag hole perimeter 146 of colostomy bag hole 122. Absorbent core 106 may be flush with the first waste channel opening 140, second waste channel opening 142, and third waste channel opening 144 to be exposed directly to environment 14 at first waste channel opening 140, second waste channel opening 142, and third waste channel opening 144. Waste spillage may directly contact absorbent core 106 in openings 140, 142, and 144 without first having to pass through a different layer. This significantly improves the ability of belt 100 to collect waste spillage, particularly in colostomy bag hole 122 where waste spillage most likely occur from the stoma.

Colostomy bag hole 122 may be an opening through liquid permeable layer 104, absorbent core 106, and liquid impermeable layer 102 to receive colostomy bag 12 and permit colostomy bag 12 to attach to the stoma. Colostomy bag hole perimeter 146 may be located at a colostomy bag hole perimeter distance 148 from belt first end 116 and colostomy bag hole 122 may have a colostomy bag hole diameter 150.

In one example, a ratio of colostomy bag hole perimeter distance 148 to belt length 119 approximately may be 1:4. This may permit attachment 138 to be positioned on the front of person 10 when colostomy bag 12 is attached to the stoma through colostomy bag hole 122. In another example, colostomy bag hole 122 may be centered within adhesive layer 108 and adhesive layer length 132 substantially may be twice colostomy bag hole diameter 150. In one example, adhesive layer length 132 approximately may be 4-inches to 6-inches.

Figure 4:
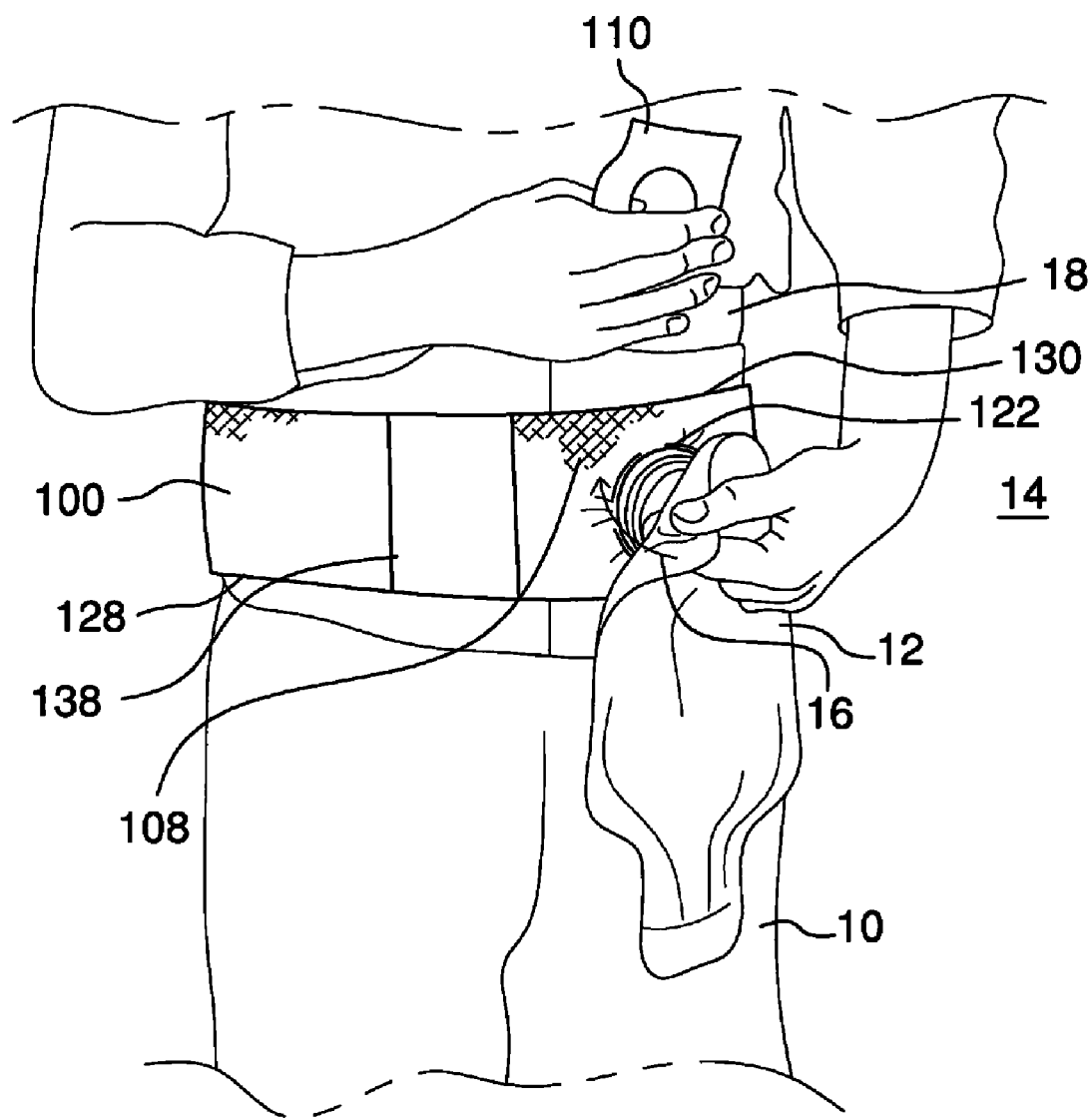
FIG. 4 is an in use view of belt 100. User 10 may hold adhesive backing 110 in a left hand.

FIG. 4 is an in use view of belt 100. User 10 may hold adhesive backing 110 in a left hand. With a right hand, user 10 may secure colostomy bag 12 through colostomy bag opening 122 and to adhesive layer 108 in a direction of arrow 16.

The terms belt top 128 and belt bottom 130 are relative since person 10 may wear belt 100 with belt bottom 130 facing towards the head of person 10 or with belt bottom 130 facing the feet of person 10. Environment 14 may include the surrounding conditions outside of person 10, belt 100, and colostomy bag 12. Typically, this may include atmosphere air. It is important that both belt top 128 and belt bottom 130 expose absorbent core 106 to environment 14 since either first waste channel opening 140 or second waste channel opening 142 may face upward, where waste spillage is more likely to be received. In addition, if the exposed absorbent core 106 facing upward through first waste channel opening 140 is filled with waste spillage, person 10 need only invert belt 100 so that unused second waste channel opening 142 is facing upward to absorb any future waste spillage. This helps extend the life of belt 100.

A used absorbent core 106 may be removed from waste channel 120 and replaced with a new, clean absorbent core 106. In addition, with absorbent core 106 removed, waste channel 120 may be cleaned adequately. Because liquid impermeable layer 102 and liquid permeable layer 104 are not connected to one another over liquid impermeable layer length 124, a user need only push together belt first end 116 and belt second end 118 to create an opening wide enough for a human hand to enter and clean waste channel 120. In addition, belt 100 may be everted (turned inside out) so that waste channel 120 forms an external loop around an interior having belt first end 116, belt second end 118, and adhesive layer 108. FIG. 5 is an isometric view of belt 100 everted and absorbent core 106 remote from belt 100. With belt 100 everted and waste channel 120 so exposed, it may be significantly easier to clean waste channel 120. If waste channel 120 instead were a sealed enclosure or included corners such as a pocket has, it would not be possible to clean waste channel 120 adequately. A person cannot reach into a sealed enclosure or reach far enough into pocket corners to clean them adequately.

When belt 100 is tightened and secure around person 10, liquid permeable layer 104 may move toward liquid impermeable layer 102 to compress absorbent core 106 and secure absorbent core 106 within waste channel 120. In one example, a liquid permeable layer length 152 (FIG. 2) of liquid permeable layer 104 as measured between belt first end 116 and belt second 118 may be shorter than liquid impermeable layer length 124 to permit liquid permeable layer 104 to move towards liquid impermeable layer 102 to compress absorbent core 106 and secure absorbent core 106 within waste channel 120 when belt 100 is tightened and secure around person 10. In another example, liquid permeable layer length 152 approximately may be 90% liquid impermeable layer length 124. This is possible since liquid permeable layer 104 is elastic. Since liquid permeable layer 104 is elastic, liquid permeable layer 104 initially may stretch to compress absorbent core 106 and subsequently may stretch to expand as absorbent core 106 collects waste spillage, an effect of which may be to squeeze absorbent core 106 with even more pressure.

The colostomy bag belt may be a device used by persons with colostomies. The colostomy bag belt may include absorbent material, similar to that used in a feminine protection pad. The colostomy bag belt may be 23 to 40 inches in length and 8 inches in width. The ends of the colostomy bag belt may incorporate matching sections of hook and loop material to secure the belt. The colostomy bag belt may include a 4- to 6-inch by 8-inch adhesive section that may be positioned around the colostomy bag.

The colostomy bag may provide a way to prevent odor and absorb the spillage from a colostomy bag. Its efficacy, ease of use, timesaving, and hygienic qualities may provide convenience, practicality, and a sense of independence. The colostomy bag may help to protect against leakage from colostomy bags. Because excess moisture may be absorbed by the colostomy bag, fewer odors may result. In addition, the colostomy bag may prevent stains to clothing, bedding, etc. Furthermore, by preventing embarrassing episodes, the colostomy bag may give the user self-confidence and appeal to anyone who utilizes colostomy bags.

The information disclosed herein is provided merely to illustrate principles and should not be construed as limiting the scope of the subject matter of the terms of the claims. The written specification and figures are, accordingly, to be regarded in an illustrative rather than a restrictive sense. Moreover, the principles disclosed may be applied to achieve the advantages described herein and to achieve other advantages or to satisfy other objectives, as well.

What is claimed is:

1. A colostomy bag belt to be worn by a person to help secure a colostomy bag to that person in an environment, the colostomy bag belt comprising:
    a liquid impermeable layer;
    a liquid permeable layer fixed against the liquid impermeable layer at a belt first end and a belt second end to form a waste channel between the belt first end, the belt second end, the liquid permeable layer, and the liquid impermeable layer, where the liquid permeable layer is elastic;
    an absorbent core located in the waste channel to absorb waste spillage from the colostomy bag and a stoma;
    an adhesive backing;
    an adhesive layer sandwiched between the liquid permeable layer and the adhesive backing, where the adhesive layer is a flat, rectangular shape layer extending from a belt top to a belt bottom, where the belt is configured to be inverted so that the belt bottom may face one of downward and upward when the colostomy bag belt is worn by a person and a colostomy bag is secured to the colostomy bag belt;
    a first hook and loop fastener attached to the liquid permeable layer at the belt first end;
    a second hook and loop fastener attached to the liquid impermeable layer at the belt second end; and
    a colostomy bag hole formed through the liquid permeable layer, the absorbent core, and the liquid impermeable layer, where the adhesive layer is positioned around the colostomy bag hole,
    where the waste channel has a first waste channel opening at the belt top extending from the belt first end to the belt second, a second waste channel opening at the belt bottom extending from the belt first end to the belt second, and a third a waste channel opening extending around a colostomy bag hole perimeter of the colostomy bag hole, where the absorbent core is flush with the first waste channel opening, the second waste channel opening, and the third waste channel opening to be exposed directly to the environment at the first waste channel opening, the second waste channel opening, and the third waste channel opening;
    where the colostomy bag hole is centered within the adhesive layer and an adhesive layer length substantially is twice a colostomy bag hole diameter of the colostomy bag hole, where the liquid impermeable layer has a liquid impermeable layer length as measured between the belt first end and the belt second end, the liquid permeable layer has a liquid permeable layer length as measured between the belt first end and the belt second end, where the liquid impermeable layer length is greater than the liquid permeable layer length, where the absorbent core includes fluff pulp, where the adhesive layer includes a liquid permeable adhesive material, and where the liquid impermeable layer includes a sealing material to act as a barrier between a wearer of the belt and waste spillage absorbed into the belt.

2. The colostomy bag belt of claim 1, where the colostomy bag hole perimeter is located at a colostomy bag hole perimeter distance from an exterior of the belt first end, where a ratio of the colostomy bag hole perimeter distance to a length of the belt approximately is 1:4.

3. The colostomy bag belt of claim 1, where the absorbent core is not attached to the liquid impermeable layer and is not attached to the liquid permeable layer.

4. A colostomy bag belt to be worn by a person to help secure a colostomy bag to that person in an environment, the colostomy bag belt comprising:
    a liquid impermeable layer;
    a liquid permeable layer fixed against the liquid impermeable layer at a belt first end and a belt second end to form a waste channel between the belt first end, the belt second end, the liquid permeable layer, and the liquid impermeable layer, where the liquid permeable layer is elastic;
    an absorbent core located in the waste channel to absorb waste spillage from the colostomy bag and a stoma, where the absorbent core fills the waste channel;
    an adhesive backing;
    an adhesive layer sandwiched between the liquid permeable layer and the adhesive backing, where the adhesive layer is a flat, rectangular shape layer extending from a belt top to a belt bottom, where the belt is configured to be inverted so that the belt bottom may face one of downward and upward when the colostomy bag belt is worn by a person and a colostomy bag is secured to the colostomy bag belt;

a first hook and loop fastener attached to the liquid permeable layer at the belt first end;

a second hook and loop fastener attached to the liquid impermeable layer at the belt second end; and a colostomy bag hole formed through the liquid permeable layer, the absorbent core, and the liquid impermeable layer, where the adhesive layer is positioned around the colostomy bag hole, where the waste channel has a first waste channel opening at the belt top extending from the belt first end to the belt second, a second waste channel opening at the belt bottom extending from the belt first end to the belt second, and a third a waste channel opening extending around a colostomy bag hole perimeter of the colostomy bag hole, where the absorbent core is flush with the first waste channel opening, the second waste channel opening, and the third waste channel opening to be exposed directly to the environment at the first waste channel opening, the second waste channel opening, and the third waste channel opening, and where the colostomy bag hole is centered within the adhesive layer and an adhesive layer length substantially is twice a colostomy bag hole diameter of the colostomy bag hole, where the absorbent core is not attached to the liquid impermeable layer and is not attached to the liquid permeable layer.

5. The colostomy bag belt of claim 4, where the colostomy bag hole perimeter is located at a colostomy bag hole perimeter distance from an exterior of the belt first end, where a ratio of the colostomy bag hole perimeter distance to a length of the belt approximately is 1:4.

6. The colostomy bag belt of claim 4, where the liquid impermeable layer has a liquid impermeable layer length as measured between the belt first end and the belt second end, the liquid permeable layer has a liquid permeable layer length as measured between the belt first end and the belt second end, where the liquid impermeable layer length is greater than the liquid permeable layer length.

7. A colostomy bag belt to be worn by a person to help secure a colostomy bag to that person in an environment, the colostomy bag belt comprising:

a liquid impermeable layer;

a liquid permeable layer fixed against the liquid impermeable layer at a belt first end and a belt second end to form a waste channel between the belt first end, the belt second end, the liquid permeable layer, and the liquid impermeable layer;

an absorbent core located in the waste channel to absorb waste spillage from the colostomy bag and a stoma;

an adhesive backing;

an adhesive layer sandwiched between the liquid permeable layer and the adhesive backing; where the belt is configured to be inverted so that the belt bottom may face one of downward and upward when the colostomy bag belt is worn by a person and a colostomy bag is secured to the colostomy bag belt;

a first hook and loop fastener attached to the liquid permeable layer at the belt first end;

a second hook and loop fastener attached to the liquid impermeable layer at the belt second end; and a colostomy bag hole formed through the liquid permeable layer, the absorbent core, and the liquid impermeable layer, where the adhesive layer is positioned around the colostomy bag hole, where the waste channel has a first waste channel opening at the belt top extending from the belt first end to the belt second, a second waste channel opening at the belt bottom extending from the belt first end to the belt second, and a third a waste channel opening extending around a colostomy bag hole perimeter of the colostomy bag hole where the absorbent core located in the waste channel fills the waste channel, where the liquid permeable layer is elastic, where the adhesive layer is a flat, rectangular shape layer extending from a belt top to a belt bottom, where the absorbent core is flush with the first waste channel opening, the second waste channel opening, and the third waste channel opening to be exposed directly to the environment at the first waste channel opening, the second waste channel opening, and the third waste channel opening.

* * * * *